(12) United States Patent
Hirschmann et al.

(10) Patent No.: US 11,541,164 B2
(45) Date of Patent: Jan. 3, 2023

(54) TAMPER EVIDENT CLOSURE CONTAINER

(71) Applicant: Plas-Tech Engineering, Inc., Lake Geneva, WI (US)

(72) Inventors: Aaron Hirschmann, Lake Geneva, WI (US); Robert Hacker, Lake Geneva, WI (US); Robert Fesus, Lake Geneva, WI (US); Christopher Grimes, Essex (GB); Hannah Talbot Aiken, Surrey (GB)

(*) Notice: Subject to any disclaimer, the term of this patent is extended or adjusted under 35 U.S.C. 154(b) by 0 days.

(21) Appl. No.: 17/840,267

(22) Filed: Jun. 14, 2022

(65) Prior Publication Data
US 2022/0305194 A1 Sep. 29, 2022

Related U.S. Application Data

(60) Division of application No. 16/506,753, filed on Jul. 9, 2019, now Pat. No. 11,357,908, which is a continuation of application No. 15/059,428, filed on Mar. 3, 2016, now Pat. No. 10,342,914, which is a continuation of application No. 14/599,202, filed on Jan. 16, 2015, now Pat. No. 9,333,289.

(51) Int. Cl.
| | | |
|---|---|---|
| *A61M 5/00* | (2006.01) | |
| *A61M 5/315* | (2006.01) | |
| *A61M 5/50* | (2006.01) | |
| *B65D 55/06* | (2006.01) | |

(52) U.S. Cl.
CPC ........ *A61M 5/002* (2013.01); *A61M 5/31501* (2013.01); *A61M 5/31525* (2013.01); *A61M 5/50* (2013.01); *B65D 55/06* (2013.01)

(58) Field of Classification Search
CPC .............. A61M 5/002; A61M 5/31501; A61M 5/31525; A61M 5/50; B65D 55/06
USPC .............. 53/443, 449, 452, 128.1, 140, 147; 206/363, 365
See application file for complete search history.

(56) References Cited

U.S. PATENT DOCUMENTS

| | | | | |
|---|---|---|---|---|
| 2,687,157 | A | * 8/1954 | Cowan | B65D 43/162 220/4.23 |
| 2,884,123 | A | 4/1959 | Dann | |
| 2,939,603 | A | * 6/1960 | Young | B65D 21/0223 206/508 |
| 2,955,705 | A | 10/1960 | Krueger et al. | |
| 3,235,069 | A | 2/1966 | Frederick | |

(Continued)

FOREIGN PATENT DOCUMENTS

| | | |
|---|---|---|
| GB | 1042411 | 9/1966 |
| WO | 2016114867 A2 | 7/2016 |

OTHER PUBLICATIONS

WIPO International Search Report and Written Opinion of the ISA for related application (PCT/US15/64707), dated Sep. 22, 2016, 7 pages, submitted previously in connection with U.S. Appl. No. 16/506,753.

(Continued)

*Primary Examiner* — Jacob K Ackun
(74) *Attorney, Agent, or Firm* — Smith Keane LLP

(57) ABSTRACT

A closure container that can house a preset drug applicator in an easily accessible manner with tamper evidencing means. The closure container contains a plurality of dosing ribs and a retainer to retain the syringe in a preset dosage amount and preferably has a window to view the barrel of the syringe.

10 Claims, 7 Drawing Sheets

(56) References Cited

U.S. PATENT DOCUMENTS

| | | | |
|---|---|---|---|
| 3,287,075 A * | 11/1966 | Batke | B65D 5/427 |
| | | | 206/509 |
| 3,407,961 A * | 10/1968 | Box | B65D 85/50 |
| | | | D30/114 |
| 3,902,621 A | 9/1975 | Hidding | |
| 4,087,018 A | 5/1978 | Tebbutt | |
| 4,432,462 A | 2/1984 | Newkirk | |
| 4,453,666 A | 6/1984 | Gordon | |
| 4,671,408 A | 6/1987 | Raines | |
| 4,979,616 A | 12/1990 | Clanton | |
| 5,031,768 A | 7/1991 | Fischer | |
| 5,039,002 A * | 8/1991 | Spamer | B65D 5/448 |
| | | | 229/199 |
| 5,090,564 A | 2/1992 | Chimienti | |
| 5,154,291 A * | 10/1992 | Sur | G11B 33/0483 |
| | | | 206/508 |
| 5,207,367 A * | 5/1993 | Dunn | B65D 83/0882 |
| | | | 206/509 |
| 5,252,664 A * | 10/1993 | Thompson | C08L 51/006 |
| | | | 525/88 |
| 5,353,929 A | 10/1994 | Foster | |
| 5,356,006 A | 10/1994 | Alpern et al. | |
| 5,358,624 A | 10/1994 | Roshdy et al. | |
| 5,368,576 A | 11/1994 | Brown et al. | |
| 5,372,254 A | 12/1994 | Gross | |
| 5,375,717 A | 12/1994 | Roshdy | |
| 5,379,900 A | 1/1995 | Gregg et al. | |
| 5,384,103 A * | 1/1995 | Miller | A61L 2/26 |
| | | | 206/508 |
| 5,392,918 A | 2/1995 | Harrison | |
| 5,395,003 A | 3/1995 | Matsuda | |
| 5,402,886 A | 4/1995 | Mcglinch | |
| 5,407,070 A | 4/1995 | Bascos et al. | |
| 5,415,287 A | 5/1995 | Hamano et al. | |
| 5,417,926 A | 5/1995 | Bouveret | |
| 5,435,448 A | 7/1995 | Kempen | |
| 5,441,152 A | 8/1995 | Estes | |
| 5,447,230 A | 9/1995 | Gerondale | |
| 5,447,231 A | 9/1995 | Kastenhofer | |
| 5,469,964 A | 11/1995 | Bailey | |
| 5,497,601 A | 3/1996 | Gonzalez | |
| 5,501,341 A | 3/1996 | Van Es | |
| 5,506,015 A | 4/1996 | Frederiksen | |
| 5,511,679 A | 4/1996 | Beck | |
| 5,526,928 A | 6/1996 | Yabe et al. | |
| 5,556,388 A | 9/1996 | Johlin, Jr. | |
| 5,564,565 A | 10/1996 | Yamada | |
| 5,566,828 A | 10/1996 | Claes et al. | |
| 5,582,599 A | 12/1996 | Daneshvar | |
| 5,607,055 A | 3/1997 | Bettinger | |
| 5,611,428 A | 3/1997 | Banerian | |
| 5,615,772 A | 4/1997 | Naganuma | |
| 5,678,719 A | 10/1997 | Adams et al. | |
| 5,690,222 A | 11/1997 | Peters | |
| 5,692,635 A | 12/1997 | Farrell et al. | |
| 5,709,310 A | 1/1998 | Kretz | |
| 5,718,334 A | 2/1998 | Demel | |
| 5,738,213 A | 4/1998 | Whiting et al. | |
| 5,758,775 A | 6/1998 | Lowe | |
| 5,758,793 A | 6/1998 | Forsyth et al. | |
| 5,765,682 A | 6/1998 | Bley et al. | |
| 5,769,222 A | 6/1998 | Banerian | |
| 5,775,498 A | 7/1998 | Kashanchi | |
| 5,792,422 A | 8/1998 | Lin et al. | |
| 5,797,510 A | 8/1998 | Carrier et al. | |
| 5,799,790 A | 9/1998 | Ziegert et al. | |
| 5,816,429 A | 10/1998 | Kobayashi | |
| 5,817,065 A | 10/1998 | Dufresne et al. | |
| 5,842,567 A | 12/1998 | Rowe et al. | |
| 5,848,691 A | 12/1998 | Morris et al. | |
| 5,848,895 A | 12/1998 | Martin et al. | |
| 5,865,335 A | 2/1999 | Farrell et al. | |
| 5,887,743 A | 3/1999 | Stahlecker et al. | |
| 5,895,374 A | 4/1999 | Slashed | |
| 5,931,332 A | 8/1999 | Mygatt et al. | |
| 5,934,498 A | 8/1999 | Jordan | |
| 5,947,284 A | 9/1999 | Foster | |
| 5,947,296 A | 9/1999 | Castora | |
| 5,950,827 A | 9/1999 | Odom et al. | |
| 5,960,956 A | 10/1999 | Langanki et al. | |
| 6,003,714 A | 12/1999 | Buermann | |
| 6,009,998 A | 1/2000 | Webinger | |
| 6,017,322 A | 1/2000 | Snoke et al. | |
| 6,036,043 A | 3/2000 | Erfgen et al. | |
| 6,036,671 A | 3/2000 | Frey | |
| 6,047,825 A | 4/2000 | Samuels | |
| 6,053,313 A | 4/2000 | Farrell et al. | |
| 6,053,905 A | 4/2000 | Daignault, Jr. et al. | |
| 6,059,107 A | 5/2000 | Slashed et al. | |
| 6,065,597 A | 5/2000 | Pettersson et al. | |
| 6,068,121 A | 5/2000 | Mcglinch | |
| 6,074,367 A | 6/2000 | Hubbell | |
| 6,089,397 A | 7/2000 | Van Melle | |
| 6,142,334 A | 11/2000 | Kristensson | |
| 6,155,420 A | 12/2000 | Phillips | |
| 6,186,325 B1 | 2/2001 | Schmidt et al. | |
| 6,228,324 B1 | 5/2001 | Hasegawa et al. | |
| RE37,252 E | 7/2001 | Hollister | |
| 6,258,078 B1 | 7/2001 | Thilly | |
| 6,279,743 B1 | 8/2001 | Ballard et al. | |
| 6,341,709 B1 | 1/2002 | Wilson | |
| 6,350,232 B1 | 2/2002 | Hascoet et al. | |
| 6,354,487 B1 * | 3/2002 | Muise, Jr. | B65D 5/0015 |
| | | | 206/508 |
| 6,357,589 B2 | 3/2002 | Schmidt et al. | |
| 6,375,006 B1 | 4/2002 | Samuels | |
| 6,401,956 B1 | 6/2002 | Heinicke et al. | |
| 6,409,717 B1 | 6/2002 | Israelsson et al. | |
| 6,415,921 B2 | 7/2002 | Ye et al. | |
| 6,478,780 B1 | 11/2002 | Shields | |
| 6,511,461 B2 | 1/2003 | Jonsson | |
| 6,547,072 B2 | 4/2003 | Whiting et al. | |
| 6,568,434 B2 | 5/2003 | Zinger | |
| 6,569,852 B1 | 5/2003 | Sodemann | |
| 6,576,918 B1 | 6/2003 | Fu et al. | |
| 6,578,709 B1 | 6/2003 | Kavanagh et al. | |
| 6,585,942 B1 | 7/2003 | Bussell et al. | |
| 6,588,588 B2 | 7/2003 | Samuels | |
| 6,595,362 B2 | 7/2003 | Penney et al. | |
| 6,604,647 B1 | 8/2003 | Luburic | |
| 6,634,498 B2 | 10/2003 | Kayerod et al. | |
| 6,669,046 B1 | 12/2003 | Sawada et al. | |
| 6,712,214 B1 * | 3/2004 | Wintermute | B65D 5/006 |
| | | | 206/745 |
| 6,719,135 B2 | 4/2004 | Armijo | |
| 6,732,858 B1 * | 5/2004 | Chang Ou | A47B 87/0276 |
| | | | 220/23.6 |
| 6,736,805 B2 | 5/2004 | Israelsson et al. | |
| 6,779,675 B2 | 8/2004 | Cousseau | |
| 6,797,973 B2 | 9/2004 | Zens | |
| 6,814,717 B2 | 11/2004 | Lin | |
| 6,822,253 B1 | 11/2004 | Martin et al. | |
| 6,848,574 B1 | 2/2005 | Israelsson et al. | |
| 6,851,568 B2 | 2/2005 | Herrmann | |
| 6,854,616 B2 | 2/2005 | Steffan | |
| 6,871,740 B1 | 3/2005 | Cao | |
| 6,884,393 B2 | 4/2005 | Hui et al. | |
| 6,890,310 B2 | 5/2005 | Fracavilla et al. | |
| 6,892,881 B2 | 5/2005 | Leitch | |
| 6,902,057 B2 | 6/2005 | Duffy | |
| 6,964,656 B2 | 11/2005 | Saint-ramon et al. | |
| 6,991,096 B2 | 1/2006 | Gottlieb et al. | |
| 6,994,823 B2 | 2/2006 | Hight, III | |
| 7,021,484 B2 | 4/2006 | Herrmann | |
| 7,028,837 B2 | 4/2006 | Yanke et al. | |
| 7,066,912 B2 | 6/2006 | Nestenborg et al. | |
| 7,104,399 B2 | 9/2006 | Duffy et al. | |
| 7,147,122 B2 | 12/2006 | Heinicke | |
| 7,160,590 B2 | 1/2007 | Vanhamel et al. | |
| 7,165,672 B2 | 1/2007 | Fago et al. | |
| 7,191,900 B2 | 3/2007 | Opie et al. | |
| 7,198,150 B1 | 4/2007 | Blaschke et al. | |
| 7,234,597 B2 | 6/2007 | Rowe et al. | |

(56) References Cited

U.S. PATENT DOCUMENTS

| | | |
|---|---|---|
| 7,261,205 B2 | 8/2007 | Cervantes |
| 7,328,792 B1 | 2/2008 | Benson |
| 7,328,794 B2 | 2/2008 | Lubs et al. |
| 7,334,678 B2 | 2/2008 | Kesler et al. |
| 7,334,679 B2 | 2/2008 | Givens, Jr. |
| 7,341,147 B2 | 3/2008 | Mallett et al. |
| 7,353,946 B2 | 4/2008 | Cervantes |
| 7,370,759 B2 | 5/2008 | Hommann |
| 7,380,658 B2 | 6/2008 | Murray et al. |
| 7,425,207 B2 | 9/2008 | Miller et al. |
| 7,434,686 B2 | 10/2008 | Prindle |
| 7,461,741 B2 | 12/2008 | State et al. |
| 7,476,223 B2 | 1/2009 | Mcbride |
| 7,490,722 B2 | 2/2009 | Mayda, II et al. |
| 7,491,176 B2 | 2/2009 | Mann |
| 7,495,246 B2 | 2/2009 | Fago et al. |
| 7,549,270 B2 | 6/2009 | Rowe et al. |
| 7,571,804 B2 | 8/2009 | Kjellmann et al. |
| 7,597,196 B2 | 10/2009 | Langone |
| 7,631,777 B1 | 12/2009 | Bukowski |
| 7,640,714 B2 | 1/2010 | Waller et al. |
| 7,678,083 B2 | 3/2010 | Stephens |
| 7,692,173 B2 | 4/2010 | Fago et al. |
| 7,694,809 B2 | 4/2010 | Garbini et al. |
| 7,694,810 B1 | 4/2010 | Barry et al. |
| 7,703,625 B2 | 4/2010 | Westphal |
| 7,708,719 B2 | 5/2010 | Wilmot et al. |
| 7,731,048 B2 | 6/2010 | Teixeira et al. |
| 7,736,341 B2 | 6/2010 | Gollobin |
| 7,743,918 B2 | 6/2010 | Itou |
| 7,755,071 B2 | 7/2010 | Polsinelli |
| 7,766,162 B2 | 8/2010 | Maki et al. |
| 7,766,163 B2 | 8/2010 | Tanghoej |
| 7,770,726 B2 | 8/2010 | Murray et al. |
| 7,798,332 B1 | 9/2010 | Brunet |
| 7,815,045 B2 | 10/2010 | Delaney et al. |
| 7,823,722 B2 | 11/2010 | Bezou et al. |
| 7,837,035 B2 | 11/2010 | Duchamp et al. |
| 7,850,646 B2 | 12/2010 | Segal |
| 7,874,426 B2 | 1/2011 | Castellani |
| 7,886,906 B1 | 2/2011 | Dunn |
| 7,886,907 B2 | 2/2011 | Murray et al. |
| 7,886,908 B2 | 2/2011 | Farrar et al. |
| 7,900,805 B2 | 3/2011 | Shelton, IV et al. |
| 7,905,352 B2 | 3/2011 | Wyrick |
| 7,918,009 B2 | 4/2011 | Fago et al. |
| 7,918,010 B2 | 4/2011 | Fago et al. |
| 7,931,167 B2 | 4/2011 | Chmeia |
| 7,942,286 B2 | 5/2011 | Shiffer et al. |
| 7,946,441 B2 | 5/2011 | Habitz et al. |
| 7,954,636 B2 | 6/2011 | Vincent-aubry |
| 8,011,505 B2 | 9/2011 | Murray et al. |
| 8,025,171 B2 | 9/2011 | Cassol et al. |
| 8,051,981 B2 | 11/2011 | Murray et al. |
| 8,052,673 B2 | 11/2011 | Nestenborg |
| 8,056,716 B2 | 11/2011 | Fonteyne et al. |
| 8,056,750 B2 | 11/2011 | Vovan |
| 8,066,141 B2 | 11/2011 | Casale et al. |
| 8,079,473 B2 | 12/2011 | Matsuda et al. |
| 8,096,414 B2 | 1/2012 | Finnestad et al. |
| 8,109,404 B2 | 2/2012 | Chmela |
| 8,113,375 B2 | 2/2012 | Jeon |
| 8,127,922 B2 | 3/2012 | Nordholm et al. |
| 8,127,961 B2 | 3/2012 | Vovan |
| 8,162,165 B2 | 4/2012 | Reed |
| 8,172,082 B2 | 5/2012 | Edwards et al. |
| 8,172,104 B2 | 5/2012 | Weber |
| 8,181,778 B1 | 5/2012 | Van Groningen et al. |
| 8,201,689 B2 | 6/2012 | Kaern |
| 8,205,745 B2 | 6/2012 | Murray et al. |
| 8,226,610 B2 | 7/2012 | Edwards et al. |
| 8,230,993 B2 | 7/2012 | Tanghoej |
| 8,235,209 B2 | 8/2012 | Peck et al. |
| 8,240,468 B2 | 8/2012 | Wilkinson et al. |
| 8,267,902 B2 | 9/2012 | Martinsson |
| 8,272,526 B1 | 9/2012 | Vovan et al. |
| 8,303,599 B2 | 11/2012 | Hess et al. |
| 8,322,555 B2 | 12/2012 | Chen |
| 8,361,026 B2 | 1/2013 | Edwards et al. |
| 8,371,467 B2 | 2/2013 | Jeon |
| 8,397,911 B1 | 3/2013 | Bauman |
| 8,434,635 B2 | 5/2013 | Wichelhaus |
| 8,448,804 B2 | 5/2013 | Luburic |
| 8,459,455 B2 | 6/2013 | Frojd |
| 8,490,790 B2 | 7/2013 | Cocheteux et al. |
| 8,499,959 B2 | 8/2013 | Chasid et al. |
| 8,517,996 B2 | 8/2013 | Fontana |
| 8,523,843 B2 | 9/2013 | Kavanagh |
| 8,534,485 B2 | 9/2013 | Van Jaarsveld |
| 8,544,645 B2 | 10/2013 | Edwards et al. |
| 8,556,105 B2 | 10/2013 | Ishii et al. |
| 8,567,602 B2 | 10/2013 | Niederberger |
| 8,568,373 B2 | 10/2013 | Kuniyasu et al. |
| 8,579,115 B2 | 11/2013 | Murphy et al. |
| 8,584,849 B2 | 11/2013 | Mccaffrey |
| 8,584,850 B2 | 11/2013 | Anderson et al. |
| 8,608,008 B2 | 12/2013 | Gingras et al. |
| 8,616,215 B2 | 12/2013 | Knajavi |
| 8,631,935 B2 | 1/2014 | Tomes et al. |
| 8,672,881 B2 | 3/2014 | Nagamatsu |
| 8,684,212 B2 | 4/2014 | Stone et al. |
| 8,684,984 B2 | 4/2014 | Bjerregaard et al. |
| 8,695,831 B2 | 4/2014 | Schick |
| 8,695,832 B2 | 4/2014 | Thielen et al. |
| 8,701,919 B2 | 4/2014 | Messier |
| 8,708,999 B2 | 4/2014 | Hong et al. |
| 8,720,685 B2 | 5/2014 | Murray et al. |
| 8,727,117 B2 | 5/2014 | Maasarani |
| 8,733,576 B2 | 5/2014 | Jeon |
| 8,734,420 B2 | 5/2014 | Ariagno et al. |
| 8,740,000 B2 | 6/2014 | Moriyama et al. |
| 8,746,484 B2 | 6/2014 | Thortensen-woll et al. |
| 8,752,722 B2 | 6/2014 | Kuhn et al. |
| 8,794,437 B2 | 8/2014 | Cervantes |
| 8,794,470 B2 | 8/2014 | Wambeke et al. |
| 8,813,955 B2 | 8/2014 | Bottger et al. |
| 9,333,289 B1* | 5/2016 | Hirschmann ..... A61M 5/31501 |
| 10,342,914 B2* | 7/2019 | Hirschmann ........... A61M 5/50 |
| 11,357,908 B2* | 6/2022 | Hirschmann ..... A61M 5/31501 |
| 2004/0069667 A1 | 4/2004 | Tomellini |
| 2006/0169611 A1 | 8/2006 | Prindle |
| 2009/0145911 A1 | 6/2009 | Hyde |
| 2009/0209031 A1 | 8/2009 | Stopek |
| 2013/0081974 A1 | 4/2013 | Hillard |
| 2013/0270137 A1 | 10/2013 | Tumminello |
| 2014/0262884 A1 | 9/2014 | Priebe et al. |
| 2014/0360903 A1 | 12/2014 | Iio |
| 2014/0367383 A1 | 12/2014 | Sellari et al. |
| 2015/0297296 A1 | 10/2015 | Stauder |
| 2016/0038713 A1 | 2/2016 | Kearns |
| 2018/0244136 A1* | 8/2018 | Schellekens ............ B32B 27/00 |

OTHER PUBLICATIONS

USPTO Office Action for related application (U.S. Appl. No. 16/506,753), dated Jul. 24, 2018, 10 pages, submitted previously in connection with U.S. Appl. No. 16/506,753.

AU Examination report for related application (2015-377191), dated Sep. 12, 2019, 3 pages, submitted previously in connection with U.S. Appl. No. 16/506,753.

Supplementary European Search Report (15878277.1-1122), dated Jan. 8, 2018, 8 pages, submitted previously in connection with U.S. Appl. No. 16/506,753.

USPTO Office Action for related application (U.S. Appl. No. 16/506,753), dated Aug. 11, 2021, 15 pages.

AU Examination report for related application (2020230336), dated May 10, 2021, 3 pages.

CA Examination report for related application (2967041), dated Feb. 1, 2022, 3 pages.

(56) References Cited

OTHER PUBLICATIONS

NZ Examination report for related application (731002), dated Jun. 3, 2022, 3 pages.

* cited by examiner

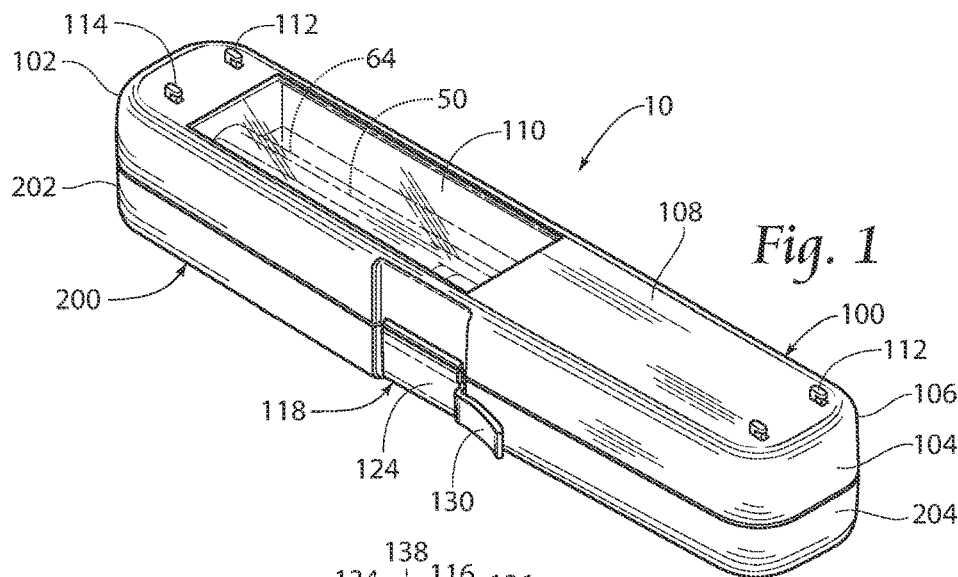
Fig. 1
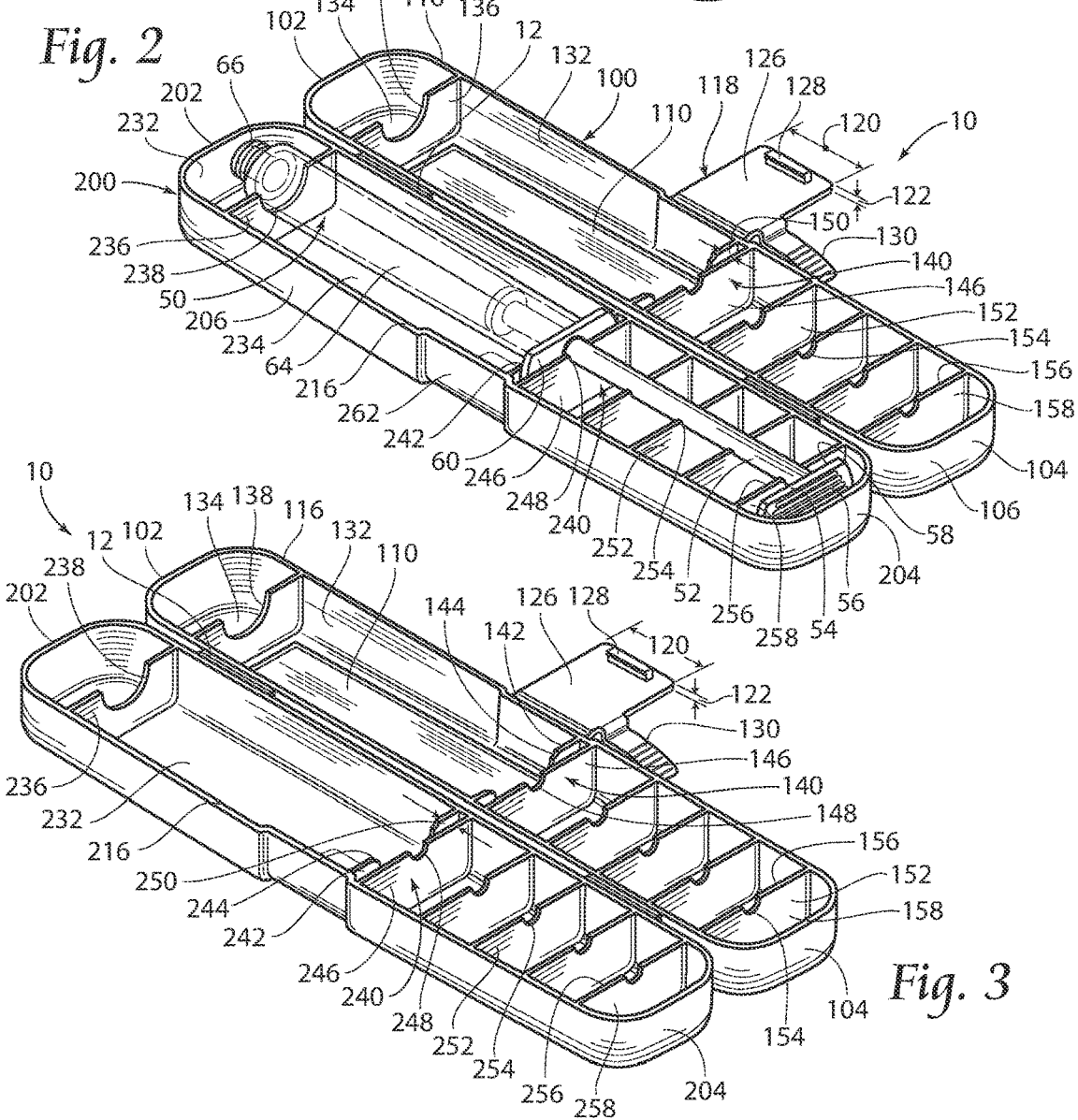
Fig. 2
Fig. 3

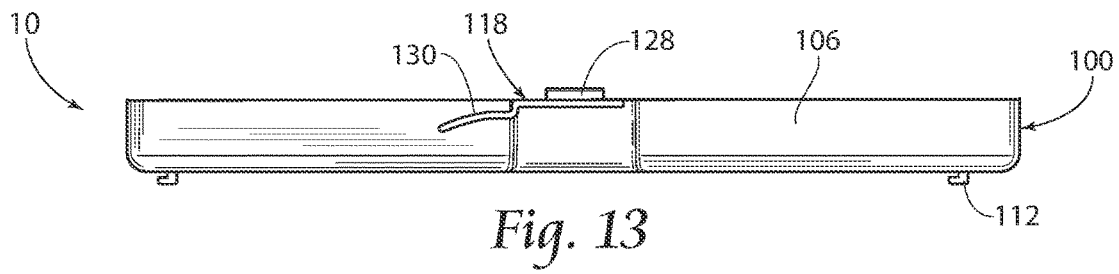
Fig. 13
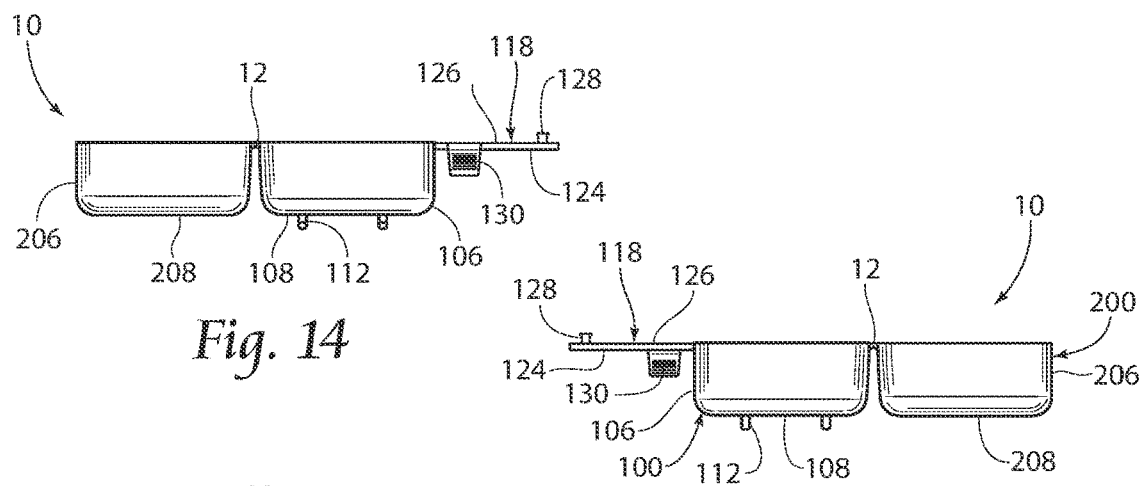
Fig. 14
Fig. 15
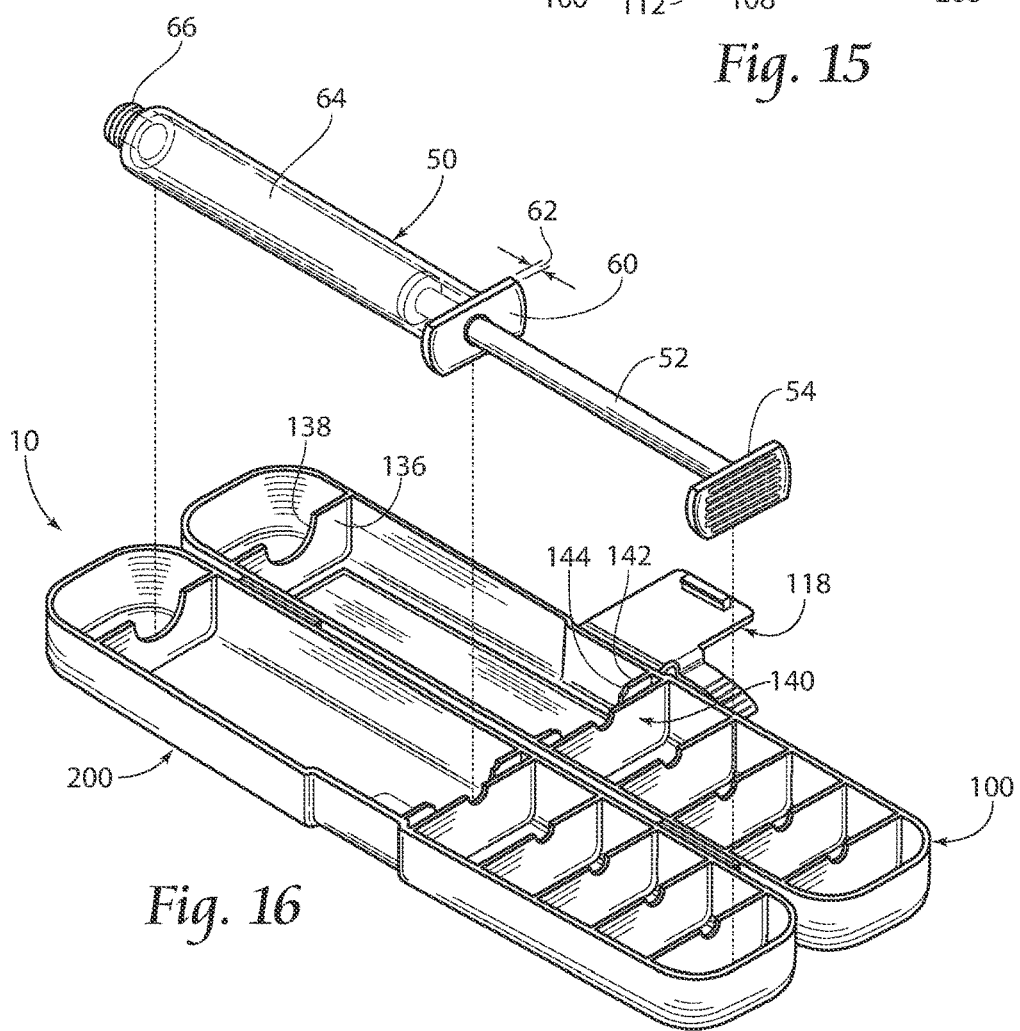
Fig. 16

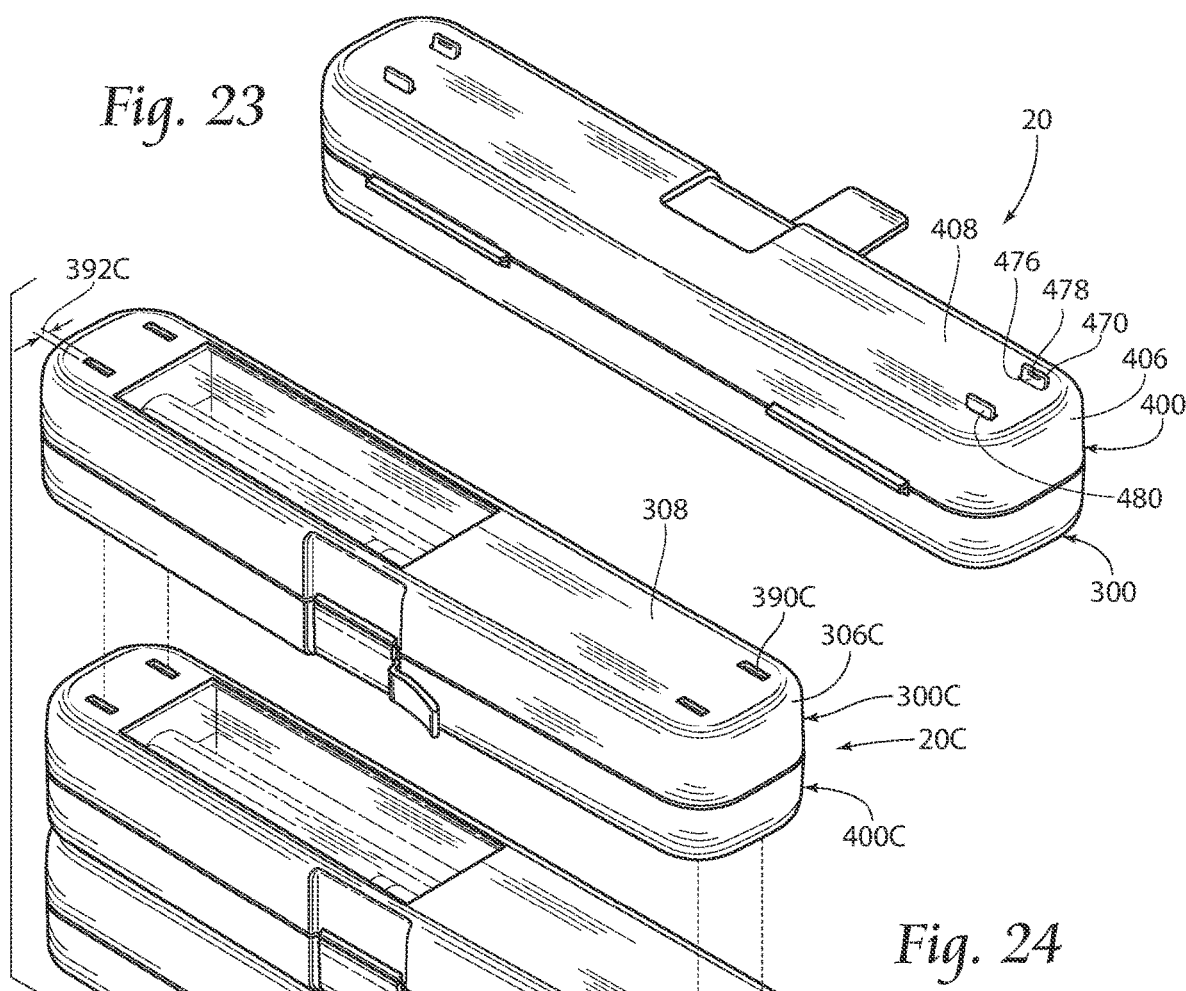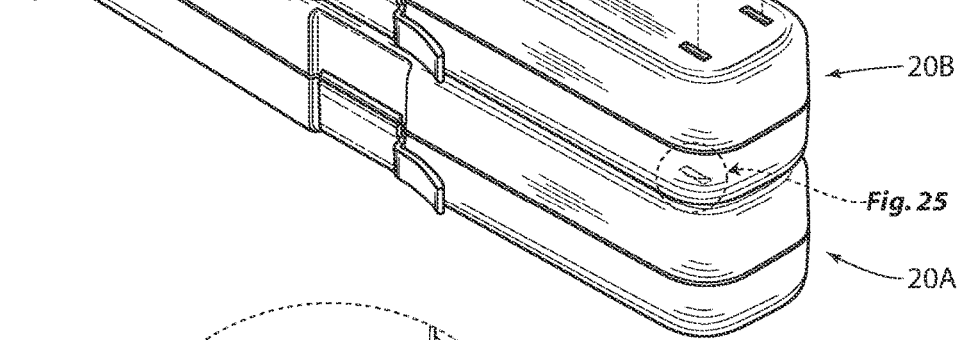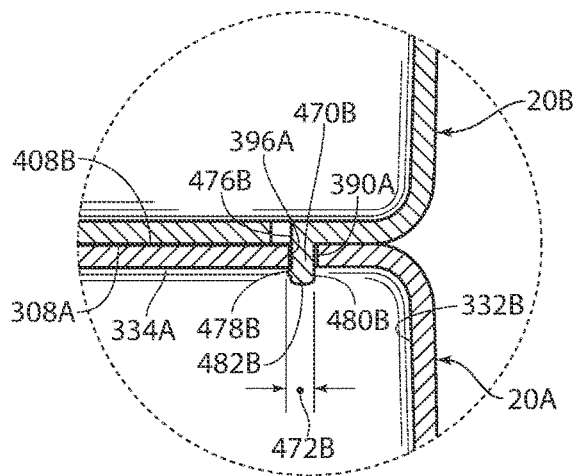

TAMPER EVIDENT CLOSURE CONTAINER

RELATED APPLICATIONS

This application is a divisional application of the co-pending U.S. patent application Ser. No. 16/506,753 filed Jul. 9, 2019 and entitled "Tamper Evident Closure Container," which is a continuation application of issued U.S. patent application Ser. No. 15/059,428 filed Mar. 3, 2016 and entitled "Tamper Evident Closure Container," now U.S. Pat. No. 10,342,914, which is a continuation application of issued U.S. patent application Ser. No. 14/599,202 filed Jan. 16, 2015 and entitled "Tamper Evident Closure Container", now U.S. Pat. No. 9,333,289, all of which are incorporated herein by reference in their entireties.

BACKGROUND OF THE INVENTION

Success rates with respect to action taken in response to an emergency situation almost always improve with proper preparation, access to the proper equipment, and speed. This could not be more true than in the case of providing a dose of fluid (e.g., epinephrine to a patient experiencing a severe or life-threatening allergic reaction (anaphylaxis)). According to the National Institute of Allergy and Infectious Diseases, early treatment with epinephrine is beneficial to patients having an anaphylactic episode because the patient could experience a rapid decline in health or death within 30 to 60 minutes. Such early treatment may also be beneficial in patients experiencing seizure activity.

In addition to quick administration of treatment, accurate dosing is crucial because not enough medicine may be ineffective and too much may cause health risks, such as dangerously high blood pressure, stroke, or death. During an anaphylactic event, for example, a health provider may need a larger or smaller dose depending on the size or age of the patient and fumbling with a vial and a needle may add precious seconds before treatment and potential dosing errors.

Further, sterilization is important whenever it comes to administering a drug to a patient through a needle and a health care provider has to know if the needle being used and the drug being administered have not been tampered with. Accordingly, the art of emergency treatment could benefit from a device that promotes quick access to a drug applicator which may be stored in pre-set doses and provides evidence of tampering.

SUMMARY OF THE INVENTION

The present invention relates to a closure container, and more particularly to a container that can house a preset drug applicator in an easily accessible manner with tamper evidencing means.

An embodiment of a method according to the present invention includes manufacturing a first casing member, a second casing member coupled to the first casing member at a hinge location, and a fastener capable of securing the first casing member to the second casing member opposite the hinge location, the fastener having a tamper evident pull tab, wherein one of the first or second casing member includes a window. The method also includes the steps of covering an area on one of the first or second casing member in which the window is to be located, treating the first or second casing member to decrease the transparency of the first or second casing member, and removing the covering to reveal the window.

According to another embodiment of a method according to the present invention, the window is transparent to visible light.

According to still another embodiment of a method according to the present invention, the treating step also includes the step of chemically etching the first or second casing member.

According to yet another embodiment of a method according to the present invention, the treating step also includes the step of mechanically etching the first or second casing member.

According to a further embodiment of a method according to the present invention, the treating step also includes the step of adding textured dies to the manufacturing process of the first or second casing member.

According to a further embodiment of a method according to the present invention, the method further includes the steps of providing a syringe containing a predetermined amount of fluid, positioning the syringe between the first casing member and the second casing member, and securing the first casing member to the second casing member, wherein at least a portion of the syringe and the predetermined amount of fluid amount are visible through the window.

An embodiment of a method according to the present invention includes manufacturing a first casing member, a second casing member, a syringe containing a predetermined amount of fluid, and a fastener having a tamper evident pull tab. In this embodiment, the first casing member includes at least one catch and the second casing member includes at least one hole configured to be mateable with a catch. The method further includes the steps of combining the above components to form a system and stacking a plurality of systems.

According to another embodiment of a method according to the present invention, the method further includes steps of configuring the at least one catch to have an L-shape profile, where a body of the catch extends perpendicularly from the first casing member and an arm of the catch extends from the body.

According to yet another embodiment of a method according to the present invention, the stacking process includes mating at least one catch of one system with at least one hole of another system.

According to still another embodiment of a method according to the present invention, the mating process means inserting the arm and body of a catch of one system into a hole of another system and sliding the systems in opposite directions relative to one another.

BRIEF DESCRIPTION OF THE DRAWINGS

FIG. 1 is a perspective view of a first embodiment of a tamper evident closure container according to the present invention.

FIG. 2 is a perspective view of the container shown in FIG. 1 in an open state and holding a syringe.

FIG. 3 is another perspective view of the container shown in FIG. 1 in an open, empty state.

FIG. 13 is a rear elevation view of the container as depicted in FIG. 3.

FIG. 14 is a right side elevation view of the container as shown in FIG. 3.

FIG. 15 is a left side elevation view of the container as depicted in FIG. 3.

FIGS. 16-19 depict a progressive method of enclosing a syringe in the first embodiment of the container according to the present invention.

FIG. 23 is a perspective view of a second embodiment of a tamper evident closure container according to the present invention.

FIG. 24 is a perspective view of a plurality of containers according to the second embodiment of the present invention stacked one on top of the other.

FIG. 25 is a cut-away view of selected section FIG. 25 of FIG. 24.

DESCRIPTION OF THE PREFERRED EMBODIMENT

Figure 4:
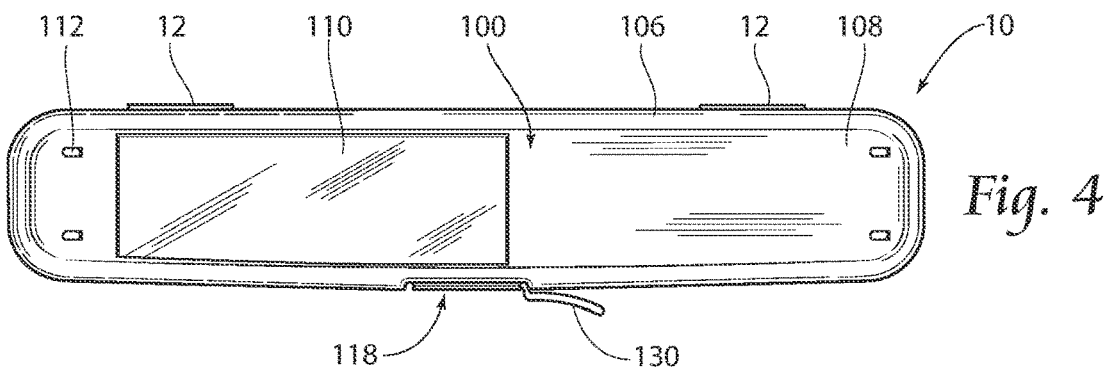
FIG. 4 is a top plan view of the container shown in FIG. 1.

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Turning first to FIG. 1, a first embodiment 10 of a closure container according to the present invention is shown. The closure container 10 preferably comprises a single injection-molded piece having a first casing member 100 hingedly attached to a second casing member 200 by at least one hinge 12 (see FIG. 2), which may be a living hinge.

The first casing member 100 may generally be formed along a longitudinal length between and including a first end 102 opposite a second end 104, an outer surface 106, a peripheral edge portion 116 (FIG. 2), a fastener 118, and an inner surface 132 (FIG. 2).

The outer surface 106 of the first casing member 100 extends from the first end 102 to the second end 104 and to the peripheral edge portion 116. The outer surface 106 has a planar portion 108 with a window 110 preferably provided therein and a plurality of catches 112 projecting therefrom.

Each catch 112 preferably has an L-shape profile and extends outward from the planar portion 108, whereby an arm 114 of the L-shape is spaced from and substantially parallel with the planar portion 108 of the outer surface 106, and all of the catches 112 are oriented preferably in the same direction.

The fastener 118 is flexibly connected at or near the peripheral edge portion 116 of the first casing member 100 opposite the hinge 12. The fastener 118 has a width 120, a thickness 122, an exterior surface 124, an interior surface 126, and a tamper-evident pull-tab 130. A barb 128 projects from the interior surface 126 distal to the outer surface 106 of the first casing member 100.

The tamper-evident pull-tab 130 preferably extends substantially perpendicular from the fastener 118 between the barb 128 and the outer surface 106 of the first casing member 100. The tamper-evident pull-tab 130 is preferably offset from the exterior surface 124 of the fastener 118 in a direction away from the container 10 when the fastener 118 is in an engaged position, as discussed further below.

The inner surface 132 of the first casing member 100 can be seen in FIGS. 2 and 3. The inner surface 132 extends from the first end 102 to the second end 104 and to the peripheral edge portion 116, and preferably has an at least substantially planar portion 134. As shown here, a bridge 136 with a notch 138 projects from the planar portion 134 of the inner surface 132 near the first end 102 to or near the peripheral edge portion 116.

A retainer 140 extends from the planar surface 134 to or near the peripheral edge portion 116 and comprises a first wall 142, with a first wall notch 144, and a second wall 146, with a second wall notch 148, substantially parallel to the first wall 142.

A plurality of dosing ribs 152 project from the planar portion 134 to or near the peripheral edge portion 116 and are spaced between the second end 104 and the second wall 146 of the retainer 140. Each dosing rib 152 has a notch 154, an innermost side 156 (hidden), and an outermost side 158. The spacing between the dosing ribs 152 relates to the predetermined dosage provided in a syringe 50 (FIG. 2) to be contained within the closure container 10. The preferable dosing amounts for which the ribs 152 will be spaced are 0.25 mL, 0.5 mL, 0.75 mL, and 1.0 mL, but other dosing amounts are contemplated.

The second casing member 200 may be seen in FIGS. 2 and 3 as well. The second casing member 200 has a first end 202 opposite a second end 204, an outer surface 206, a peripheral edge portion 216, and an inner surface 232.

Figure 5:
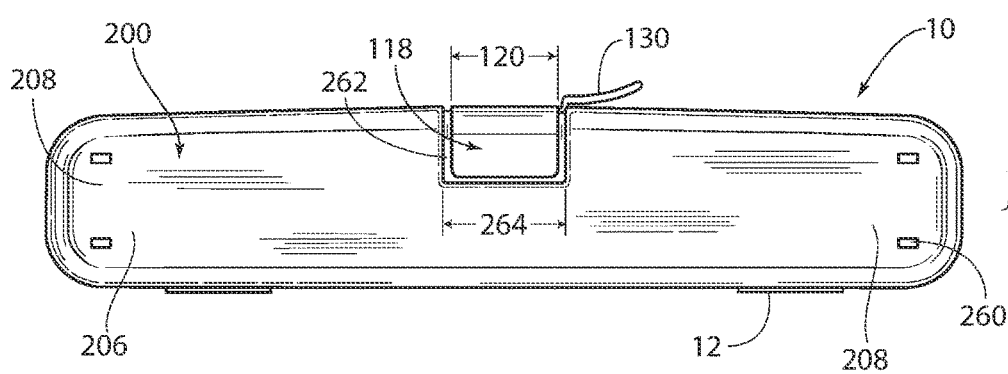
FIG. 5 is a bottom plan view of the container shown in FIG. 1.
Figure 6:
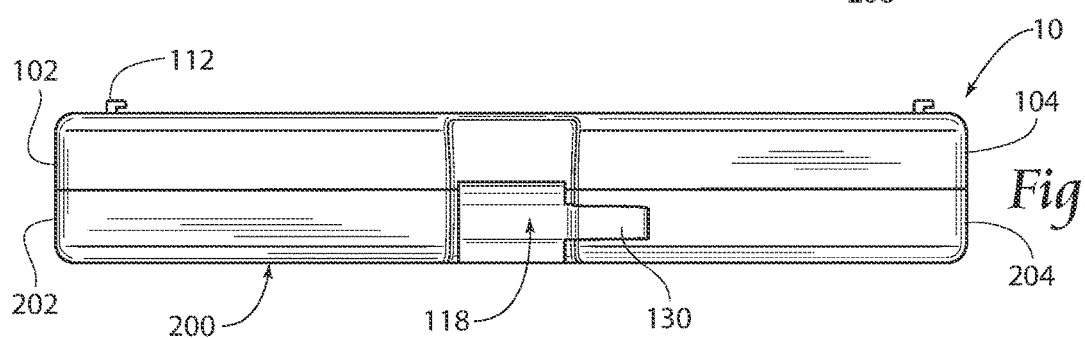
FIG. 6 is a front elevation view of the container shown in FIG. 1.
Figure 7:
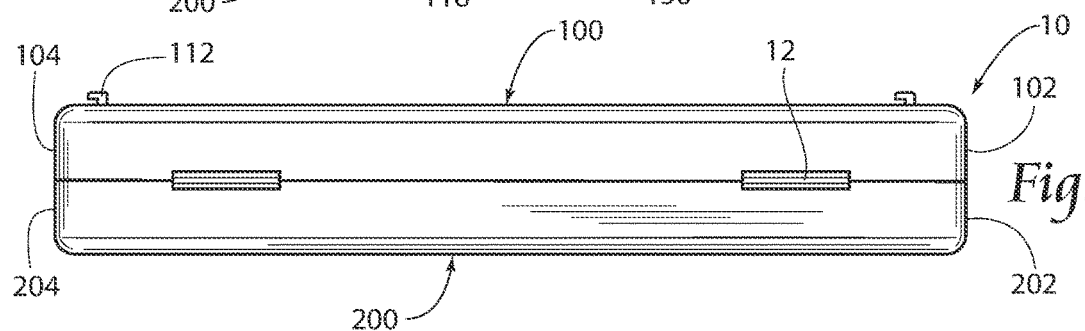
FIG. 7 is a rear elevation view of the container shown in FIG. 1.
Figure 8:
FIG. 8 is a right side elevation view of the container shown in FIG. 1.
Figure 9:
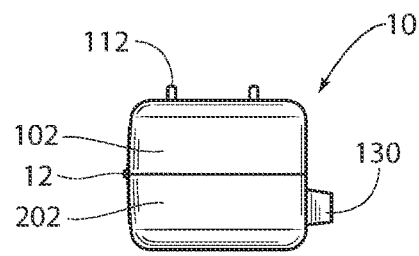
FIG. 9 is a left side elevation view of the container shown in FIG. 1.

The outer surface 206 of the second casing member 200 extends from the first end 202 to the second end 204 and to the peripheral edge portion 216. The outer surface 206 preferably has an at least substantially planar portion 208 with a plurality of holes 260 (FIG. 5) therein which are sized, positioned, and configured to be mateable with the catches 112 of the first casing member 100 of another closure container 10.

Figure 10:
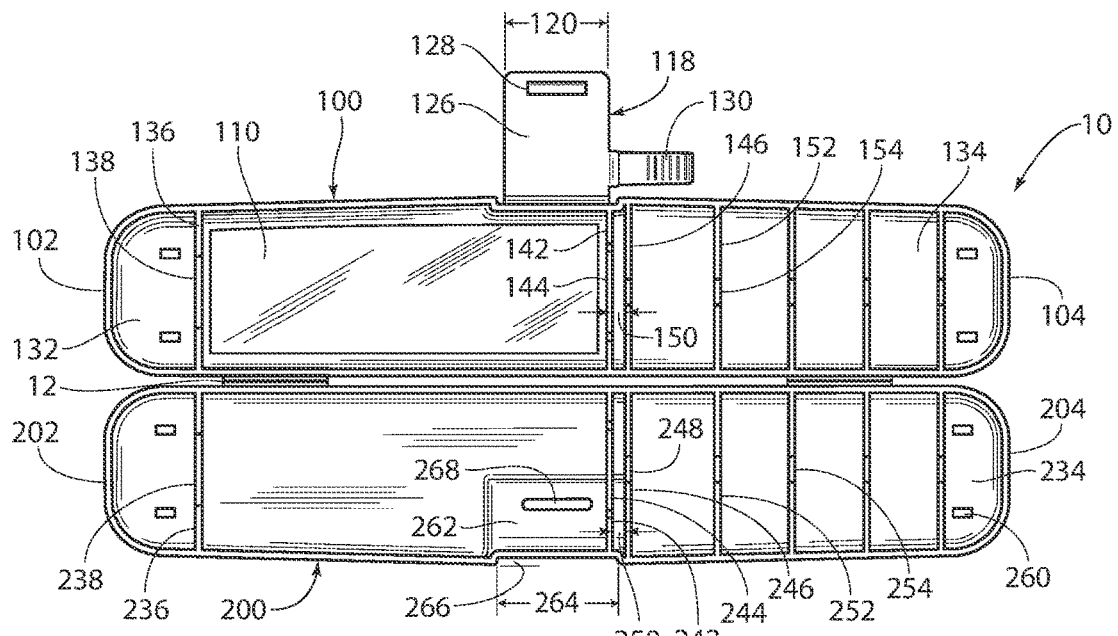
FIG. 10 is a top plan view of the container as shown in FIG. 3.
Figure 11:
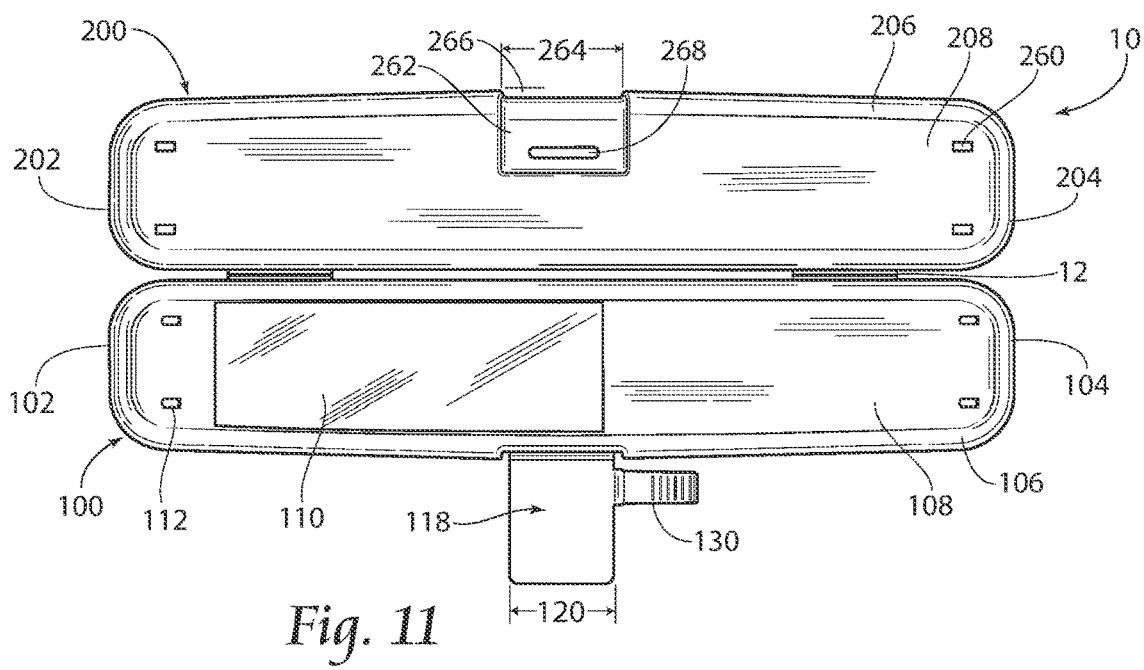
FIG. 11 is a bottom plan view of the container as depicted in FIG. 3.
Figure 12:
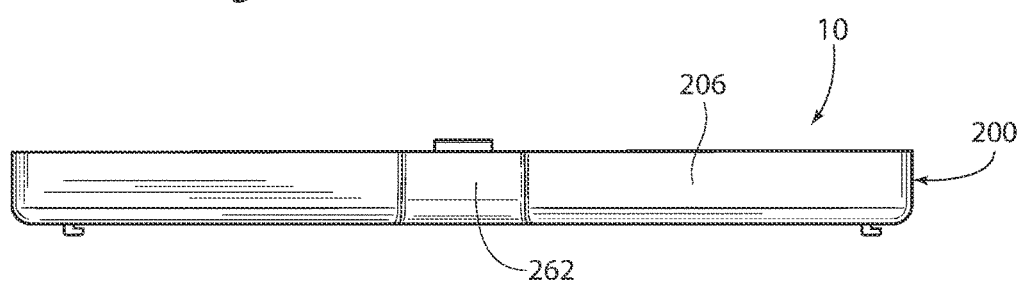
FIG. 12 is a front elevation view of the container as shown in FIG. 3.

As shown in FIGS. 10 and 11, the outer surface 206 of the second casing member 200 has a recess 262 with a width 264 slightly greater than the width 120 of the fastener 118 and a depth 266 preferably similar to the thickness 122 of the fastener 118. A slot 268 sized and configured to receive the barb 128 of the fastener 118 is provided within the recess 268.

Looking back to FIGS. 2 and 3, the inside surface 232 of the second casing member 200 is shown. The inside surface 232 of the second casing member 200 is preferably substantially similar to the inside surface 132 of the first casing member 100. As shown here, the inner surface 232 extends from the first end 202 to the second end 204 and to the peripheral edge portion 216, and preferably has a planar portion 234. As shown here, a bridge 236 with a notch 238 projects from the planar portion 234 of the inner surface 232 near the first end 202 to or near the peripheral edge portion 216.

A retainer 240 extends from the planar portion 208 to or near the peripheral edge portion 216 and comprises a first wall 242, with a first wall notch 244, and a second wall 246, with a second wall notch 248, substantially parallel to the first wall 242. The first wall 242 is spaced apart from the second wall 246 a distance 250.

A plurality of dosing ribs 252 project from the planar portion 234 of the inner surface 232 to or near the peripheral edge portion 216 and are spaced between the second end 204 and the second wall 246 of the retainer 240. Each dosing rib 252 has a notch 254, an innermost side 256, and an outermost side 258. The spacing between the dosing ribs 252 relates to the predetermined dosage provided in a syringe 50 (FIG. 2) to be contained within the closure container 10. The preferable dosing amounts for which the ribs 252 will be spaced are 0.25 mL, 0.5 mL, 0.75 mL, and 1.0 mL, however, other dosing amounts are contemplated.

Additionally or alternatively, the dosing ribs 152 of the first casing member 100 may be staggered from the dosing ribs 252 of the second casing member 200 to provide more dosing options while still providing secure support of the syringe 50 and the plunger 52.

Additionally or alternatively, the first casing member 100 or the second casing member 200 may not contain the respective dosing ribs, retainer, or the bridge; instead being configured simply to cover the other casing member 200, 100.

Looking back to FIG. 1 and also to FIGS. 4-9, the closure container 10 is depicted in from various views with the syringe 50 positioned within the container 10 and the fastener 118 engaged with the second casing member 200. As shown, when the container 10 is in a closed position, the fastener 118 preferably resides substantially within the recess 262, with the barb 128 received within the slot 268.

The material from which the closure container 10 is formed is preferably initially transparent. The window 110 is preferably formed by covering the area in which the window 110 will be located, treating at least the outer surfaces 106,206 of the first casing member 100 and the second casing member 200, respectively, to decrease the transparency of those surfaces, and removing the covering to reveal the window 110. The treatment may be performed by any process now known or later discovered, including but not limited to, chemical etching, mechanical etching (e.g., sand blasting), or during the molding process using textured dies.

Continuing to look at FIG. 1, a syringe 50 can be viewed through the window 110 in a pre-set dosage configuration, ready for use. The window 110 is preferably located at least radially outward from the barrel 64 of the syringe 50 to provide a care provider with a view of the syringe 50 and preferably the dosage amount provided in the barrel 64 without having to open the closure container 10.

Figure 17:
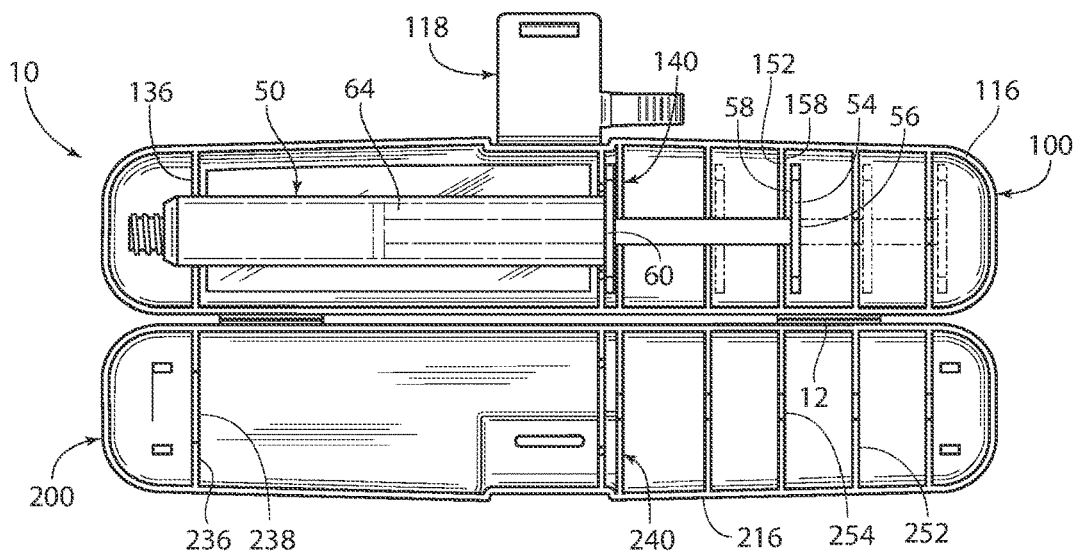

Directing attention to FIGS. 16-19, the installation of the syringe 50 into the container 10 is shown. FIG. 16 illustrates the syringe 50 with a predetermined dosage provided in the barrel 64 prior to placement within the second casing member 200; however, the syringe 50 may be placed within the first casing member 100 as well, as shown in FIG. 17.

Looking to FIG. 17, with reference to FIG. 16, the flange 60 of the syringe 50 is placed within the retainer 140 of the first casing member 100 with a portion of the barrel 64 received by the notch 144 of the first wall 142 and another portion of the barrel 64 received by the notch 138 of the bridge 136. Preferably, the distance 150 between the first and second walls 142,146 of the retainer 140 (FIG. 10) is preferably slightly greater than the thickness 62 of the syringe flange 60.

The top 54 of the plunger 52 has a topside surface 56 and an underside surface 58. When installed within the container 10, the underside surface 58 of the syringe top 54 preferably resides against or near the outermost side 158 of the respective dosing rib 152. The placement of the flange 60 within the retainer 140 and the top 54 against the dosing rib 152 reduces the likelihood that the syringe 50 will be accidentally discharged prior to use.

Figure 18:
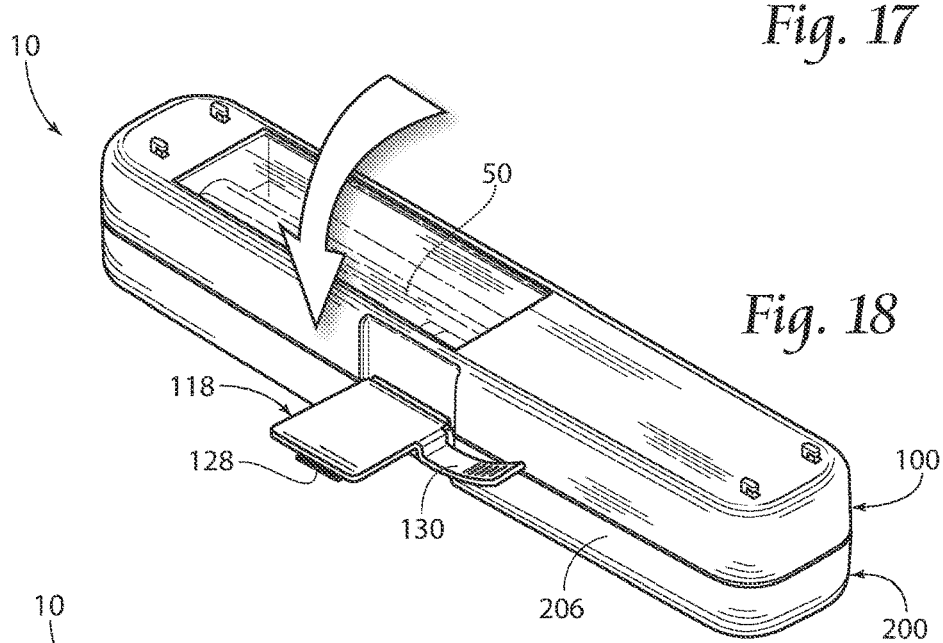

FIG. 18 illustrates the closing of the container 10 with the first and second casing members 100,200 rotating about the hinge 12 (FIG. 17) and adjoining the first casing member peripheral edge portion 116 (FIG. 17) with the second casing member peripheral edge portion 216 (FIG. 17). The barrel 64 of the syringe 50 is thereby also received within the bridge notch 238, the retainer 240, and the respective dosing rib notch 254 of the second casing member 200 (see FIG. 17).

Figure 19:
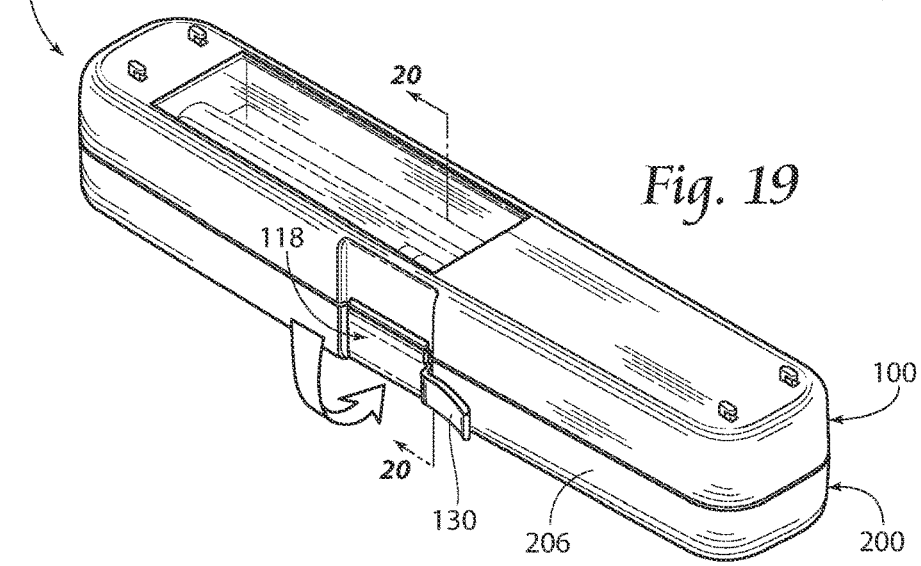
Figure 20:
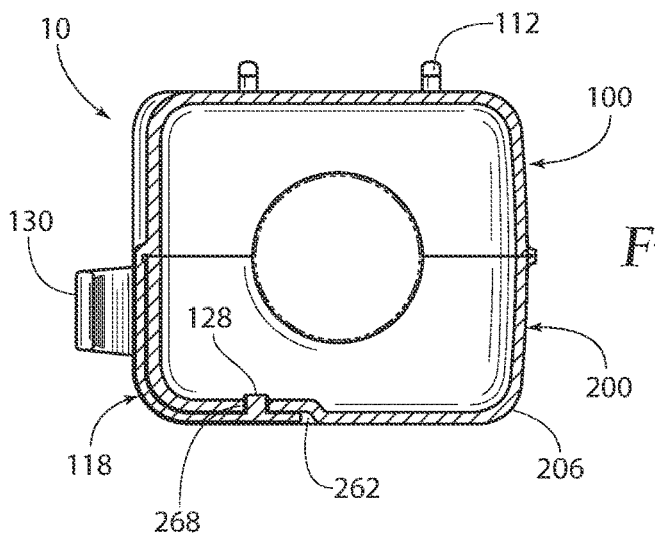
FIG. 20 is a cross-sectional view along line 20-20 of FIG. 19.

Looking to FIGS. 19 and 20, the engagement of the fastener 118 is shown. The fastener 118 is wrapped around the outside surface 206 of the second casing member 200 within the recess 262. The barb 128 is engageably received within the slot 268 to retain the fastener 118 in the engaged position.

When the time comes for the syringe 50 to be removed from the container 10, the health care personnel will pull the tamper-evident pull-tab 130 away from the container 10 which will tear through the fastener 118 and sever the fastener's connection between the first and second casing members 100,200, thus allowing the container 10 to be opened and the syringe 50 to be removed.

Removal of the tamper-evident pull-tab 130 permanently detaches at least a portion of the fastener 118 from the first casing member 100 when pulled to gain access to the syringe 50. Therefore, tampering with the fastener 118 or the tamper-evident pull-tab in an attempt to gain access to the syringe 50 will be visibly noticeable by a tear in the fastener 118.

Figure 22:
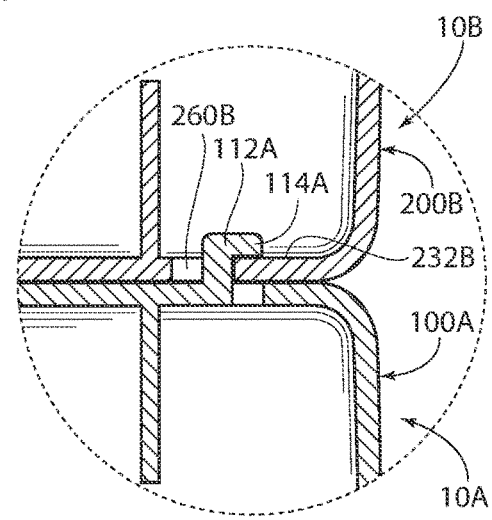
FIG. 22 is a selected cut-away view of FIG. 21.
Figure 21:
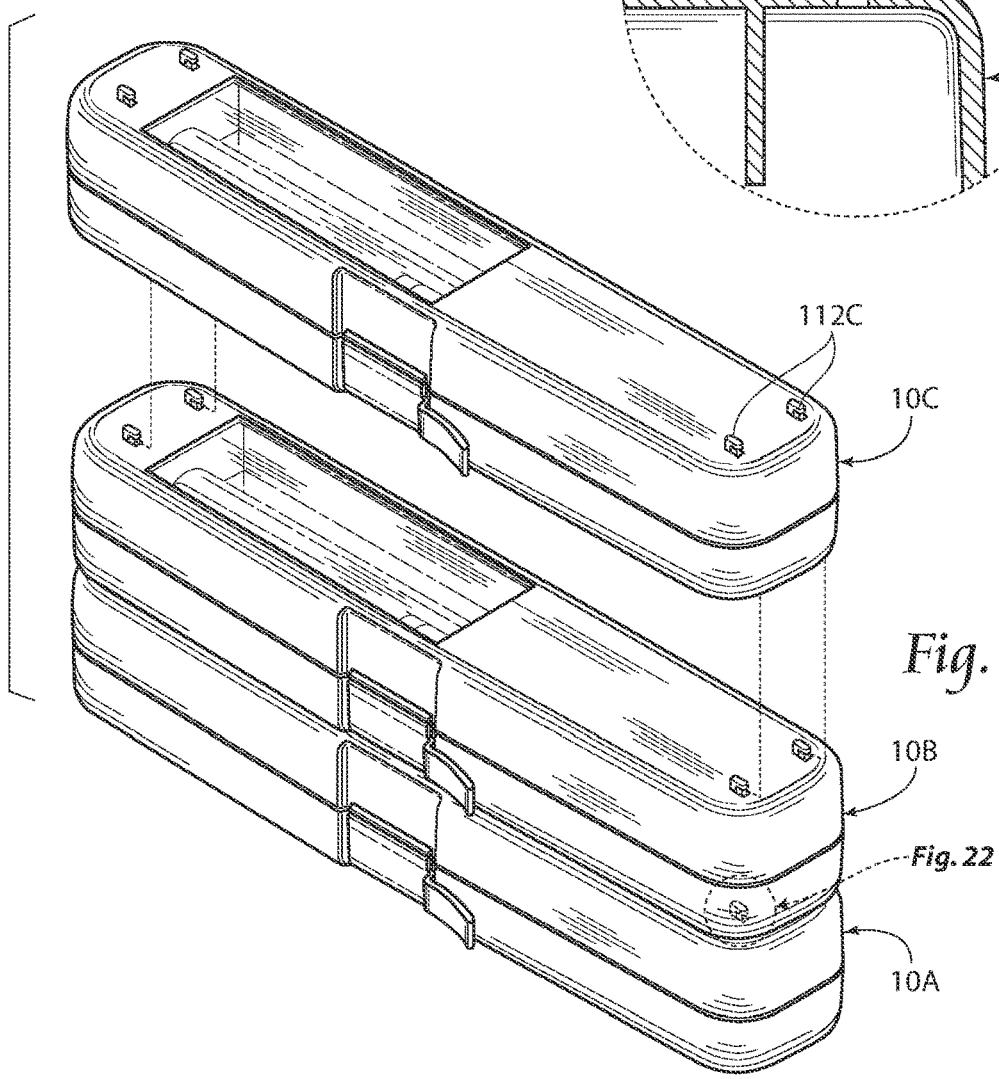
FIG. 21 is a perspective view of a plurality of containers according to the first embodiment of the present invention stacked one on top of the other.

FIGS. 21 and 22 demonstrate how multiple containers 10A,10B,10C may be stacked one on top of the other.

As shown in greater detail in FIG. 22, a mateable stacking interaction between a catch 112A and a hole 260B is shown. The interaction allows the containers 10A,10B to be removably interlocked. The catch 112A, along with the other three catches (not shown), of the first container 10A are inserted within the holes 260B of the second container 10B and the containers 10A,10B, are slid in opposite directions relative to one another to place the arm 114A of the first container 10A adjacent to the inner surface 232B of the second container second casing member 200B. These actions are depicted by the dashed lines in FIG. 21.

FIG. 23 illustrates a second embodiment 20 of the closure container according to the present invention. The closure container 20 has tabs 470 projecting from the planar portion 408 of the second casing member outer surface 406 and apertures 390 (FIG. 24) provided through the planar portion 308 of the first casing member outer surface 306. The apertures 390 are alignable and mateable with the tabs 470 of a corresponding closure container 20.

Each tab 470 has a width 472 (FIG. 24), an inward face 476, and an outward face 480. The tabs 470 preferably extend substantially perpendicular away from the outside surface planar portion 408 and comprise a protuberance 478, or similarly shaped protrusion, on the inward face 476 at or near the distal end portion 482 (FIG. 25) of each tab 470.

Alternatively, it is contemplated that the protuberance 478 may protrude from the outward face 480.

The apertures 390 have a width 392 and an abutting surface 396. The width 392 of the apertures 390 is preferably slightly greater than the width 472 of the tabs 470.

FIGS. 24 and 25 demonstrate how multiple containers 20A, 20B, 20C may be stacked by inserting the tabs 470B of a second container 20B within the apertures 390A of a first container 20B. This action is depicted by the dashed lines in FIG. 24. In this fashion, stacking of these embodiments 20 require only a singular directional movement, rather than the compound movement that may be utilized to stack cases according to the first embodiment 10.

FIG. 25 more closely illustrates the interaction between a tab 470B of the second container 20B is received within an aperture 390 of the first container 20A to provide a releasable connection between the two containers 20A, 20B. Preferably, the inner face 476B of the tab 470B is substantially flush with the abutting surface 396A of the aperture 390A, whereby the protuberance 478B of the tab 470B is in contact with the planar portion 334A of the first casing member inner surface 332A and the first container's second casing member outer surface planar portion 308A is flush with the second container's first casing member outer surface planar portion 408B.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A method comprising the steps of:
   manufacturing a first casing member, a second casing member coupled to the first casing member at a hinge location, and a fastener capable of securing the first casing member to the second casing member opposite the hinge location, the fastener having a tamper evident pull tab, wherein one of the first or second casing member includes a window;
   covering an area on one of the first or second casing member in which the window is to be located;
   treating the first or second casing member to decrease the transparency of the first or second casing member; and
   removing the covering to reveal the window.

2. The method of claim 1, wherein the window is transparent to visible light.

3. The method of claim 1, the treating step further comprising the step of:
   chemically etching the first or second casing member.

4. The method of claim 1, the treating step further comprising the step of:
   mechanically etching the first or second casing member.

5. The method of claim 1, the treating step further comprising the step of:
   adding textured dies to the manufacturing process of the first or second casing member.

6. The method of claim 1, further comprising the step of:
   providing a syringe containing a predetermined amount of fluid;
   positioning the syringe between the first casing member and the second casing member; and
   securing the first casing member to the second casing member, wherein at least a portion of the syringe and the predetermined amount of fluid amount are visible through the window.

7. A method comprising the steps of:
   manufacturing a first casing member, a second casing member, a syringe containing a predetermined amount of fluid, and a fastener having a tamper evident pull tab, wherein the first casing member includes at least one catch and the second casing member includes at least one hole configured to be mateable with a catch;
   combining the above components to form a system; and
   stacking a plurality of systems.

8. The method of claim 7, the manufacturing step further comprising:
   configuring the at least one catch to have an L-shape profile, wherein a body of the catch extends perpendicularly from the first casing member and an arm of the catch extends from the body.

9. The method of claim 7, the stacking step further comprising:
   mating at least one catch of one system with at least one hole of another system.

10. The method of claim 9, the mating step further comprising:
    inserting the arm and body of a catch of one system into a hole of another system; and
    sliding the systems in opposite directions relative to one another.

* * * * *